United States Patent
Dieckmann et al.

(10) Patent No.: US 8,198,403 B2
(45) Date of Patent: Jun. 12, 2012

(54) DIAMETER-SELECTIVE REVERSIBLE CLOSABLE PEPTIDES

(75) Inventors: Gregg R. Dieckmann, Plano, TX (US);
Alfonzo Ortiz-Acevedo, El Paso, TX (US); Ray Baughman, Dallas, TX (US);
Alan B. Dalton, Shamley Green (GB);
Rockford K. Draper, Plano, TX (US);
Inga H. Musselman, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 578 days.

(21) Appl. No.: 11/441,480

(22) Filed: May 26, 2006

(65) Prior Publication Data

US 2007/0269364 A1 Nov. 22, 2007

Related U.S. Application Data

(60) Provisional application No. 60/685,449, filed on May 26, 2005.

(51) Int. Cl.
*C01B 31/00* (2006.01)
*C07K 7/06* (2006.01)
*C07K 7/08* (2006.01)
*D01F 9/12* (2006.01)

(52) U.S. Cl. ........ 530/317; 530/326; 530/327; 530/345; 977/746; 977/845; 977/847

(58) Field of Classification Search .................. None
See application file for complete search history.

(56) References Cited

U.S. PATENT DOCUMENTS

| | | | | |
|---|---|---|---|---|
| 6,277,818 | B1* | 8/2001 | Mazar et al. | 514/9 |
| 7,189,405 | B1* | 3/2007 | Rice et al. | 424/249.1 |
| 2004/0022718 | A1* | 2/2004 | Stupp et al. | 423/445 R |
| 2005/0009039 | A1* | 1/2005 | Jagota et al. | 435/6 |
| 2005/0107289 | A1* | 5/2005 | Ghadiri et al. | 514/9 |
| 2007/0243554 | A1* | 10/2007 | Jagota et al. | 435/7.1 |

OTHER PUBLICATIONS

Bachilo, S. M.; et al., "Structure-Assigned Optical Spectra of Single-Walled Carbon Nanotubes," Science 2002, 298:2361-2366.
Baughman, R. H.; et al., "Carbon Nanotubes—the Route Toward Applications," Science 2002, 297:787-792.
Bong, D. T.; et al., "Self-Assembling Organic Nanotubes," Angew. Chem. Int. Ed. 2001, 40:988-1011.
Boul, P. J.; et al., "Reversible sidewall functionalization of buckytubes," Chem. Phys. Lett. 1999, 310, 367-372.
Chattopadhyay, D.; et al., "A Route for Bulk Separation of Semiconducting from Metallic Single-Wall Carbon Nanotubes," J. Am. Chem. Soc. 2003, 125, 3370-3375.
Dalton, A. B.; et al., "A Functional Conjugated Polymer to Process, Purify and Selectively Interact with Single Wall Carbon Nanotubes," J. Synth. Met. 2001, 121, 1217-1218.
Dieckmann, G. R.; et al., "Controlled Assembly of Carbon Nanotubes by Designed Amphiphilic Peptide Helices," J. Am. Chem. Soc. 2003, 125, 1770-1777.
Doorn, S. K.; et al., "High Resolution Capillary Electrophoresis of Carbon Nanotubes," J. Am. Chem. Soc. 2002, 124, 3169-3174.

(Continued)

*Primary Examiner* — Jeffrey E Russel

(74) *Attorney, Agent, or Firm* — Winstead PC

(57) ABSTRACT

The present invention includes compositions and methods for the isolation, separation and chelation of Carbon Nanotubes (CNTs) using a cyclizable peptide.

4 Claims, 4 Drawing Sheets

OTHER PUBLICATIONS

Doorn, S. K.; et al., "Capillary Electrophoresis Separations of Bundled and Individual Carbon Nanotubes," J. Phys. Chem. B 2003, 107, 6063-6069.

Duesberg, G. S.; et al., "Chromatographic size separation of single-wall carbon nanotubes," Appl. Phys. A: Mater. Sci. Process. 1998, 67, 117-119.

Duesberg, G. S.; et al., "Chromatography of Carbon Nanotubes," Syn. Met. 1999, 103, 2484-2485.

Farkas, E.; et al., "Length sorting cut single wall carbon nanotubes by high performance liquid chromatography," Chem. Phys. Lett. 2002, 363, 111-116.

Ghadiri, M. R.; et al., "Self-assembling organic nanotubes based on a cyclic peptide architecture," Nature 1993, 366, 324-327.

Heller, D. A.; et al., "Concomitant Length and Diameter Separation of Single-Walled Carbon Nanotubes," J. Am. Chem. Soc. 2004, 126, 14567-14573.

Karachevtsev, V. A.; et al., "Raman spectroscopy of HiPCO single-walled carbon nanotubes at 300 and 5 K," Carbon 2003, 41, 1567-1574.

Moore, V. C.; et al., "Individually Suspended Single-Walled Carbon Nanotubes in Various Surfactants," Nano Lett. 2003, 3, 1379-1382.

Nagahara, L. A.; et al., "Mica etch pits as a height calibration source for atomic force microscopy," Vac. Sci. Technol. B. 1994, 12, 1694-1697.

Nikolaev, P.; et al., "Gas-phase catalytic growth of single-walled carbon nanotubes from carbon monoxide," Chem. Phys. Lett. 1999, 313, 91-97.

O'Connell, M. J.; et al., "Reversible water-solubilization of single-walled carbon nanotubes by polymer wrapping," Chem. Phys. Lett. 2001, 342, 265-271.

Okamoto, H.; et al., "Variety of the Molecular Conformation in Peptide Nanorings and Nanotubes," J. Am. Chem. Soc. 2003, 125, 2756-2769.

Ortiz-Acevedo, A.; et al., "Synthesis of reversible cyclic peptides," Tet. Lett. 2004, 45, 6795-6798.

Strano, M. S.; et al., "Understanding the Nature of the DNA-Assisted Separation of Single-Walled Carbon Nanotubes Using Fluorescence and Raman Spectroscopy," Nano Lett. 2004, 4, 543-550.

Wang, S.; et al., "Peptides with selective affinity for carbon nanotubes," Nat. Mat. 2003, 2, 196-200.

Zheng, M.; et al., "DNA-assisted dispersion and separation of carbon nanotubes," Nat. Mat. 2003, 2, 338-342.

Zheng, M.; et al., "Structure-Based Carbon Nanotube Sorting by Sequence-Dependent DNA Assembly," Science 2003, 302, 1545-1548.

Zorbas, V.; et al., "Preparation and Characterization of Individual Peptide-Wrapped Single-Walled Carbon Nanotubes," J. Am. Chem. Soc. 2004, 126, 7222-7227.

\* cited by examiner

Figure 7 head-tail only head-head or tail-tail

Figure 8

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (4)..(4)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (10)..(10)
<223> OTHER INFORMATION: D-amino acid

<400> SEQUENCE: 1

Tyr Ala Lys Ala Lys Ala Lys Ala Lys Ala Gln
1               5                   10

<210> SEQ ID NO 2
<211> LENGTH: 15
<212> TYPE: PRT
<213> ORGANISM: Artificial sequence
<220> FEATURE:
<223> OTHER INFORMATION: Description of Artificial Sequence: Synthetic
```

```
        amino acid sequence
<220> FEATURE:
<221> NAME/KEY: MISC_FEATURE
<222> LOCATION: (2)..(2)
<223> OTHER INFORMATION: D-maino acid
<220> FEATURE:
<221> NAME/KEY: MISC_FEATURE
<222> LOCATION: (4)..(4)
<223> OTHER INFORMATION: D-maino acid
<220> FEATURE:
<221> NAME/KEY: MISC_FEATURE
<222> LOCATION: (6)..(6)
<223> OTHER INFORMATION: D-maino acid
<220> FEATURE:
<221> NAME/KEY: MISC_FEATURE
<222> LOCATION: (8)..(8)
<223> OTHER INFORMATION: D-maino acid
<220> FEATURE:
<221> NAME/KEY: MISC_FEATURE
<222> LOCATION: (10)..(10)
<223> OTHER INFORMATION: D-maino acid
<220> FEATURE:
<221> NAME/KEY: MISC_FEATURE
<222> LOCATION: (12)..(12)
<223> OTHER INFORMATION: D-maino acid
<220> FEATURE:
<221> NAME/KEY: MISC_FEATURE
<222> LOCATION: (14)..(14)
<223> OTHER INFORMATION: D-maino acid

<400> SEQUENCE: 2

Tyr Ala Lys Ala Lys Ala Lys Ala Lys Ala Lys Ala Lys Ala Gln
1               5                   10                  15
```

DIAMETER-SELECTIVE REVERSIBLE CLOSABLE PEPTIDES

CROSS-REFERENCE TO RELATED APPLICATIONS

This application claims priority to 60/685,449, filed May 26, 2005, the entire contents of which are incorporated herein by reference.

STATEMENT OF FEDERAL GOVERNMENT SUPPORT

This invention was made with U.S. Government support under a Contract awarded by the MIRROR Federal Initiative. The government may own certain rights in this invention.

TECHNICAL FIELD OF THE INVENTION

The present invention relates in general to the field of nanotechnology and, more particularly, to compositions and methods for the isolation and manipulation of nanomaterials using diameter-selective reversible closable peptides.

BACKGROUND OF THE INVENTION

Without limiting the scope of the invention, its background is described in connection with Carbon nanotubes (CNTs).

Carbon nanotubes have novel electrical and mechanical properties with potential biological applications ranging from sensors to tissue supports to artificial muscles (1). Various agents, e.g., surfactants (ref. 2 and references therein), polymers (refs 3 and 4, and references therein), polypeptides (5, 6 and references therein), and nucleic acids (7, 8)) have been used to disperse CNTs, however, two major hurdles exist that limit the usefulness of CNTs in many applications. First, current preparative methods for CNTs generate heterogeneous nanotube mixtures that can vary in length, diameter and electronic type (semiconducting, semimetallic and metallic). This heterogeneity ultimately limits the utility of the CNT materials. Recent work on the length (4, 9-13), diameter (7, 8, 14) and concomitant length and diameter (15) separation of CNTs, however, has provided important advances in the area of nanotube purification. Second, unmodified CNTs are very hydrophobic, readily aggregate, and are therefore difficult to interface with biological materials. Detergents like sodium dodecyl sulfate (SDS) that are commonly used to solubilize CNTs in water would likely disrupt cellular membranes and are incompatible with many biological applications, while covalent modification of CNTs with soluble moieties (16, 17) interferes with CNT properties.

What are needed are compositions and methods for the isolation, separation, characterization and functionalization of CNTs. These compositions and methods must be highly selective, rapid and inexpensive. Furthermore, the compositions and methods should be made from easily available materials that are not harmful to the environment. In fact, in some cases it will be very useful to use these compositions and methods to isolate and even chelate CNTs.

SUMMARY OF THE INVENTION

The present invention includes compositions and methods for making and using a cyclic peptide that binds specifically a single-walled carbon nanotube. The peptide may be reversibly or even irreversibly cyclized. One example of a closable peptide is an amphiphilic peptide, which may include alternating L- and D-amino acids. Alternatively, the peptide may include, e.g., typical amino acid monomer building blocks and/or mixtures and combinations of amino acids and other building blocks (e.g., alpha-hydroxy acids) that yield non-traditional peptide backbones when assembled together (e.g., peptidomimetics). The peptide may even include non-native amino acids, that is, amino acids that have non-natural side chains, including modified side chains or even side chains that are modified post-translationally or post-synthesis. Therefore, the peptides may be chemically synthesized in whole or in part by chemical synthesis and/or may be synthesized in whole or in part by using ribosomes in vivo or in vitro.

The cyclizable peptide may include two or more terminal groups that can form covalent or noncovalent linkage(s) within the peptide to create a closed ring structure. One example of a cyclizable peptide may include both N- and C-termini that are derivatized with thiol groups. Alternatively, the peptide may have the N-terminus as a free amine and the C-terminus as a free acid group such that they can form an amide bond and close the ring. The peptide may be used to solubilize carbon single-walled nanotubes.

The cyclic peptide may be cyclized in a reversible manner by reducing and oxidizing thiol groups that are at the ends of the peptide and/or internal to the peptide. In fact, the same peptide may be cyclized at multiple locations by providing thiol groups either in side chains and/or at the N- and/or the C-end. One example of a peptide has the sequence: $R_1$—Y($^P$AK)$_4$$^P$AQ-NH—$R_2$, (SEQ ID NO.: 1) wherein $R_1$ and $R_2$ comprise thiol or other groups. Another example of a peptide has the sequence: $R_1$—Y($^P$AK)$_6$$^P$AQ-NH—$R_2$, (SEQ ID NO.: 2) wherein $R_1$ and $R_2$ comprise thiol or other groups.

Yet another example of the present invention includes a carbon nanotube separating agent that is an amphiphilic helical peptide that specifically binds a single-walled carbon nanotube. The peptide noncovalently binds the single-walled carbon nanotube and may further include a substrate to which the peptides are attached, e.g., a glass, a quartz, a silicon, a bead, a gel, a polymer, a column and the like. For example, the peptides may themselves be crosslinked to form a polymer. The peptides may also include one or more sidegroups that are derivatized for crosslinking. In one example, the reversible cyclic peptide includes alternating L- and D-amino acids with N- and C-termini derivatized thiol groups.

The present invention also includes a method of capturing single-walled carbon nanotubes by mixing single-walled carbon nanotubes with one or more cyclized peptide comprising at least two thiol groups. Examples of peptide for use with the method of the present invention include, e.g., a peptide named RC5: $R_1$—Y($^P$AK)$_4$$^P$AQ-NH—$R_2$ (SEQ ID NO.: 1); and/or RC7: $R_1$—Y($^P$AK)$_6$$^P$AQ-NH—$R_2$ (SEQ ID NO.: 2).

Other examples of the present invention include: a single-walled carbon nanotube purified by diameter selection using a cyclized peptide with at least two thiol groups. A single-walled carbon nanotube purification system may include a substrate with one or more cyclized peptides that bind specifically and non-covalently to a single-walled carbon nanotube having a specific diameter. Examples of substrates include: a bead, a gel, a polymer, a glass, a quartz, a silicon, a ceramic, a plastic, a protein, a nucleic acid, a carbohydrate, a lipid and mixtures and combinations thereof.

The present invention may also include one or more of the following: (1) a closable peptide with at least two thiol groups, wherein the peptide binds single-walled carbon nanotubes; (2) a carbon nanotube separating agent that has an amphiphilic closable peptide that binds specifically a single-walled carbon nanotube; (3) a chelating agent with a cycliz-

BRIEF DESCRIPTION OF THE DRAWINGS

For a more complete understanding of the features and advantages of the present invention, reference is now made to the detailed description of the invention along with the accompanying figures and in which:

FIGS. 5A to 5D are graphs of (5A and 5B) Raman RBM regions of RC5/SWNT (5A) and RC7/SWNT (5B) dispersions (red, 16 k×g, 20 min; blue, 100 k×g, 1 hr; 633 nm excitation); FIGS. 5C and 5D are comparisons of RBM regions of RC5/SWNT (red) and RC7/SWNT (blue) dispersions excited at 633 nm (5C) and 488 nm (5D);

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Reversible cyclic peptides (RCPs) with alternating L- and D-amino acids with N- and C-termini derivatized with thiol-containing groups allowing reversible peptide cyclization—to solubilize and noncovalently functionalize carbon single-walled nanotubes (SWNTs) in aqueous solution. Solubilization occurs through wrapping of RCPs around the circumference of a SWNT, followed by the formation of head-to-tail covalent bonds, yielding closed rings on the nanotubes. By controlling the length of the RCPs limited diameter-selective solubilization of the SWNTs was demonstrated as revealed by UV/Vis/NIR and Raman spectroscopies, as well as atomic force microscopy.

To improve CNT solubility in water and biocompatibility, a family of amphiphilic helical peptides was developed that noncovalently bind and solubilize single-walled carbon nanotubes (SWNTs) in water, yielding unbundled, individual SWNTs (5, 18). Although these helical peptides are excellent solubilization agents, there are two peptide properties that we would like to improve: (1) their affinity for CNTs, and (2) the selectivity of CNT solubilization, based either on nanotube type or size. The class of peptides described herein may covalently close around the circumference of CNTs. Encircling CNTs with peptides has two major advantages. One is that the peptides will not dissociate from the CNTs, so they provide extremely stable CNT dispersions. The second is that CNTs can be preferentially solubilized when the nanotube diameter is small enough to be encircled by a given length peptide, thereby enabling diameter-selective separation of SWNTs.

One example of the novel class of peptides are cyclic peptides containing alternating L- and D-amino acids (AAs) (19, 20) called reversible cyclic peptides (RCPs)(21) for the diameter-selective solubilization of HiPco SWNTs (FIG. 1A). In L/D-peptides, all side chains reside on one face of the backbone, encouraging a ring-like conformation with the side chains on the ring exterior. In addition, our cyclic peptides have N- and C-termini that are derivatized to contain thiol groups, allowing reversible peptide cyclization through a disulfide bond (FIG. 1A). These results demonstrate that peptides with different N-to-C-terminal lengths wrap around SWNTs have sufficiently small diameters to cause selective enrichment of small diameter CNTs dispersed in solution.

Figure 1:
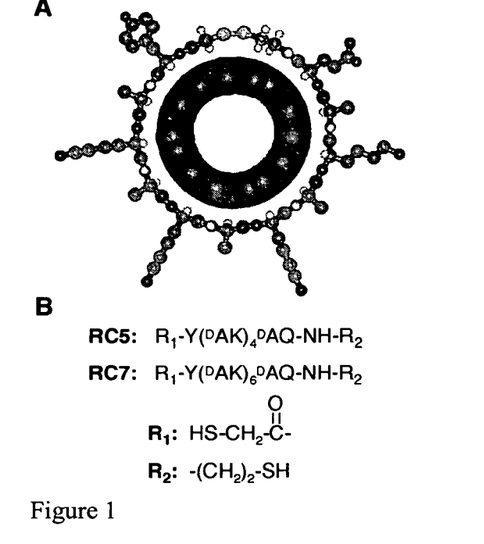
FIG. 1A (top) is a model (end-on view) of RC5 with a (11,3) SWNT (C, green; H, white; N, blue; O, red; S, yellow; SWNT, pink)
FIG. 1B shows the RC5 and RC7 sequences.

Peptide Design. Computer-aided modeling used the software packages InsightII and Discover (Accelrys Inc.; San Diego, Calif.). The diameter distribution for the HiPco SWNTs used for these studies was previously reported to be 0.7 to 1.4 nm (22). To determine the appropriate RCP ring sizes that would selectively encircle CNTs in the 0.7 to 1.4 nm range, model (11, 3) and (14, 5) SWNT structures with diameters of 1.01 and 1.35 nm, respectively, were created from atomic coordinates obtained from www.pa.msu.edu/cmp/csc/nanotube.html. When the van der Waals radii are taken into account, the SWNT diameters are 1.15 and 1.49 nm, respectively. Diameters including van der Waals radii were used to design RCPs of lengths that, when closed into rings, would form pores capable of selectively encircling CNTs of different diameters (FIG. 1). The RCPs were generated using backbone dihedral angles reported previously for standard cyclic peptides (23).

Peptide/CNT Solution Preparation. The peptides RC5 and RC7 were synthesized and purified following previously published methods (21). Unpurified SWNTs, produced by the method of high-pressure disproportionation of carbon monoxide (HiPco process), were obtained from Carbon Nanotechnologies, Inc., and used without modification. Ultra pure deionized (DI) water was degassed under high vacuum and heating to remove dissolved oxygen that would promote disulfide bond formation in peptide solutions. Degassed DI water was used to prepare all solutions. The concentrations of RCP stock solutions were determined by UV absorbance spectroscopy utilizing the absorbance of the tyrosine residue in each RCP ($\epsilon=1420$ $M^{-1}$ $cm^{-1}$ at 275 nm). The concentration of free thiol in solution was determined by reacting an aliquot of peptide solution with 5,5'-dithiobis(2-nitrobenzoic acid) (DTNB) in 0.1 M sodium phosphate buffer, pH 8 (Ellman test (24)), and comparing the resulting $A410$ ($\epsilon=13650$ M-1 cm-1) to a reference solution. The Ellman test was used to determine the free thiol concentration of stock solutions as well as to monitor the oxidation of experimental solutions.

Peptide/SWNT dispersions were prepared by sonicating 1 mL of solution containing HiPco SWNTs (~30 μg) and peptide at a desired concentration. Sonication was performed for specified times using a VWR Scientific Branson Sonifier 250 horn sonicator with a 5 Watt input energy to the solutions. The dispersions were then centrifuged, and the supernatant was used for all analyses.

UV/is/NIR Spectroscopy. RCP/SWNT dispersions were prepared as described above, with the exception that $D_2O$ was used instead of $H_2O$. Absorption spectra were obtained using a Perkin-Elmer Lamda 900 UV-Vis-NIR spectrophotometer and quartz cells having a 1 cm path length. Spectra were collected every nm between 200 and 1600 nm.

Figure 7:
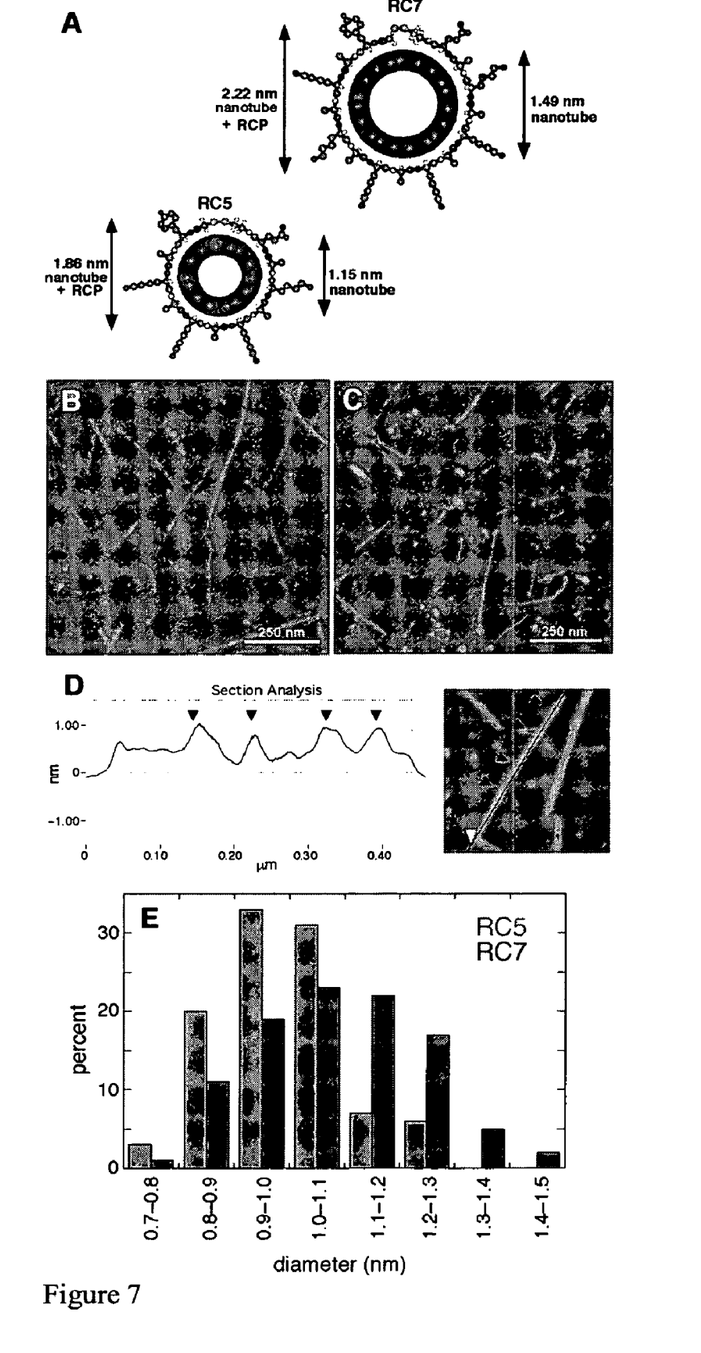
FIG. 7A shows the expected dimensions for RC5/SWNT and RC7/SWNT structures.
FIGS. 7B and 7C are 1.0×1.0 µm AFM images of diluted 100 k×g RC5/SWNT (7B) and RC7/SWNT (7C) dispersions.
FIG. 7D (left) is an AFM height profile taken along the length of a single nanotube (7D, right AFM image, 0.5×0.5 µm), showing the differences between the smooth and beaded areas (beaded areas indicated by arrows).
FIG. 7E shows the measured diameter distributions (smooth regions) for diluted 100 k×g RC5/SWNT and RC7/SWNT dispersions (n=100; four 2.0×2.0 µm images, two samples for each peptide)

Raman Spectroscopy. Samples for Raman analysis were prepared as follows. A 100 μM peptide solution was vortexed with two equivalents of tris(2-carboxyethyl)-phosphine HCl (TCEP; Pierce Biotechnology, Inc.; Rockford, Ill.) for 10 min prior to sonication with HiPco SWNTs. Centrifugation was then carried out in the following sequence: a first spin at 16 k×g for 20 min; the supernatant was placed through a second spin for 30 min at 50 k×g; finally the supernatant from the second spin was placed through a third spin for 60 min at 100 k×g. The final RCP/SWNT supernatant (~2 μL) was spotted on a SpectRim substrate (Tienta Sciences, Inc.; Indianapolis, Ind.) and allowed to dry in a dessicator overnight prior to Raman analysis. Drying RCP/SWNT dispersions prepared by high-speed centrifugation did not induce the formation of RCP/SWNT bundles on substrates, as demonstrated by AFM of the dried material (FIG. 7), similar to previous results with other peptide/SWNT dispersions studied (18). Thus, drying does not make bundles that could influence the Raman spectra. For samples containing SDS, no TCEP was added.

Dispersive Raman spectra were recorded on a Jobin Yvon Horiba high resolution LabRam Raman microscope system. The laser excitation was provided by a Spectra-Physics model 127 helium-neon laser operating at 633 nm with 20 mW output power (laser in resonance with both metallic and semiconducting CNTs), using a 10× objective lens and a 25 μm slit. The laser power at the sample was ~8 mW and was focused to ~1 μm. Wavenumber calibration was carried out using the 520.5 $cm^{-1}$ line of a silicon wafer. The spectra of peptide/SWNT and SDS/SWNT dispersions were recorded by scanning the 50 to 2000 $cm^{-1}$ region for a total acquisition time of 8 min.

Atomic Force Microscopy (AFM). Samples were prepared as described in the Raman section. The 100 k×g supernatants were diluted 10-fold with degassed DI water, and 10 μL volumes were dropped onto freshly cleaved muscovite mica (Asheville-Schoonmaker Mica Co.). Samples were placed in a dessicator to dry for 24 h prior to AFM imaging. AFM images (2.0×2.0 μm) were acquired in air under ambient conditions using a Digital Instruments, Inc. Nanoscope III Multimode Scanning Probe Microscope operated in the TappingMode™ with 5.0 N $m^{-1}$ force constant cantilevers and a reduced Z-limit (100 V)(18). The AFM scanner was calibrated using a NanoDevices, Inc., standard of lines with 2 μm pitch and 20 nm height, dimensions similar to those of SWNTs. The height calibration was verified to be 0.3% accurate using hydrofluoric acid etched pits in muscovite mica where 2 nm steps are observed along the long axis and 1 nm steps are observed along the short axis (25).

RCP Design. The appropriate peptide lengths for wrapping SWNTs of different diameters were determined using computer models of RCPs encircling SWNTs. Optimized RCP models suggest that peptides with 11 amino acids (40 backbone atoms) and 15 amino acids (52 backbone atoms) should be sufficient to encircle SWNTs with diameters of 1.15 and 1.49 nm, respectively. An additional 7 atoms per peptide come from modifications to the N- and C-termini, yielding the peptides RC5 and RC7 (FIG. 1B). The resulting RCPs contain two free thiols, which enable the formation of closed rings upon intramolecular reactions to create disulfide bonds. Both RC5 and RC7 reversibly convert between reduced (linear) and oxidized (cyclized) states, with monomers being the predominant form in a 100 μM peptide solution (21).

Figure 2:
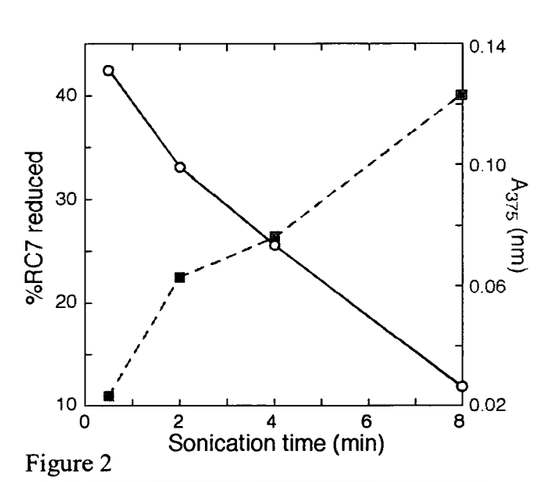
FIG. 2 is a graph that shows the percent reduced RC7 (Left axis, red solid line) in dispersion as a function of sonication time (measured by Ellman test) and on the Right axis, blue dotted line, the $A_{375}$ for RC7/SWNT dispersion as a function of sonication time.

SWNT Solubilization by RCPs. The solubilization of HiPco SWNTs by RC5 and RC7 was studied by sonicating SWNTs in the presence of aqueous RCP solutions and monitoring the SWNT absorbance at 375 nm to determine the amount of dispersed SWNTs. With a reduced (linear) RCP solution, a black dispersion formed, characteristic of SWNTs in solution, for which $A_{375}$ intensified with increased sonication time (FIG. 2). This increase in SWNT concentration with increased sonication time also correlated with a decrease in reduced RCP as measured by the Ellman test (FIG. 2); taken together, these results suggest that sonication leads to peptide oxidation (cyclization) with concurrent CNT solubilization.

Figure 3:
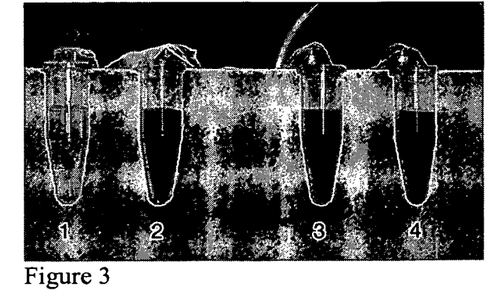
FIG. 3 shows the oxidation state of: (Tube 1) RC5 initially oxidized (cyclized), sonicated in presence of SWNTs; (Tube 2) RC5 initially reduced (linear), oxidized in presence of SWNTs; (Tube 3) RC7 initially oxidized (cyclized), sonicated in presence of SWNTs; (Tube 4) RC7 initially reduced (linear), oxidized in presence of SWNTs.

The amount of SWNTs solubilized also depends on whether the RCP is in the linear (reduced) or cyclized (oxidized) form. When the RCP was initially open, high levels of SWNT solubilization occurred after sonication (FIGS. 2 and 3); however, solubilization was significantly less efficient with RCPs that were initially in the cyclized state (FIG. 3). The small amount of CNTs observed in vials 1 and 3 of FIG. 3 may be due to weak interactions between Lys side chains on each RCP exterior and the CNTs; RC5 (vial 1) has fewer Lys residues than RC7 (vial 3), so under the same conditions the longer peptide should yield a slightly higher nanotube solubilization. When control peptides were used that have the same AA sequence as the RCPs but lack terminal thiol groups, less SWNT solubilization occurred FIG. 2 is a graph that shows the Percent reduced RC7 in dispersion as a function of sonication time (Left axis, red solid line) (measured by Ellman test) and, on the Right axis, blue dotted line, $A_{375}$ for RC7/SWNT dispersion as a function of sonication time (data not shown). In addition, when β-mercaptoethanol was added to an RCP/SWNT dispersion to disrupt RCP disulfides, a majority of the SWNTs precipitated out of solution (data not shown). Furthermore, dilution of RCP/SWNT dispersions with water resulted in minimal SWNT precipitation, suggesting that the RCPs were very tightly bound to SWNTs as predicted if the RCPs were covalently closed around the CNTs. Taken together, these data strongly suggest that RCPs solubilize and stabilize SWNTs in aqueous solution by wrapping around the circumference of the CNTs, forming rings closed by disulfide bonds.

FIG. 3 shows the oxidation state of: (Tube 1) RC5 initially oxidized (cyclized), sonicated in presence of SWNTs; (Tube 2) RC5 initially reduced (linear), oxidized in presence of SWNTs; (Tube 3) RC7 initially oxidized (cyclized), sonicated in presence of SWNTs; (Tube 4) RC7 initially reduced (linear), oxidized in presence of SWNTs. For all samples, a 4 min sonication time was used, followed by 16 k×g centrifugation for 10 min.

Figure 4:
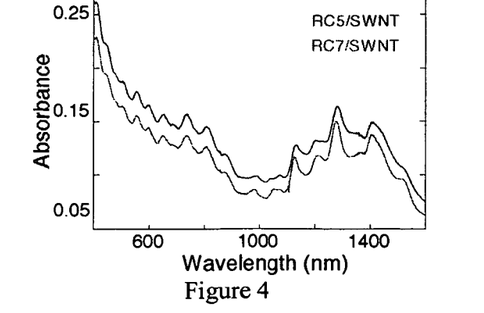
FIG. 4 is a graph that shows the UV/Vis/NIR spectra of RC5/SWNT (red, lower spectrum) and RC7/SWNT (blue, upper spectrum) dispersions.

Optical Spectroscopy. The optical absorption spectra of RC5/SWNT and RC7/SWNT dispersions show multiple well-defined peaks from the visible to NIR regions (FIG. 4). The peaks represent optical transitions between singularities for a specific type of tube (n, m) and are evidence that RCPs efficiently debundle HiPco SWNTs. Moreover, for a given peptide concentration, dispersions made with RC7 reproducibly absorb more strongly than those made with RC5. Each RCP, when cyclized, should solubilize all individual SWNTs with diameters smaller than the cyclized peptide's inner pore. Since RC7 is longer, its inner pore when cyclized should be larger and so should solubilize a larger population of SWNTs than cyclized RC5, giving rise to the higher absorbance observed in FIG. 4.

Figure 5:
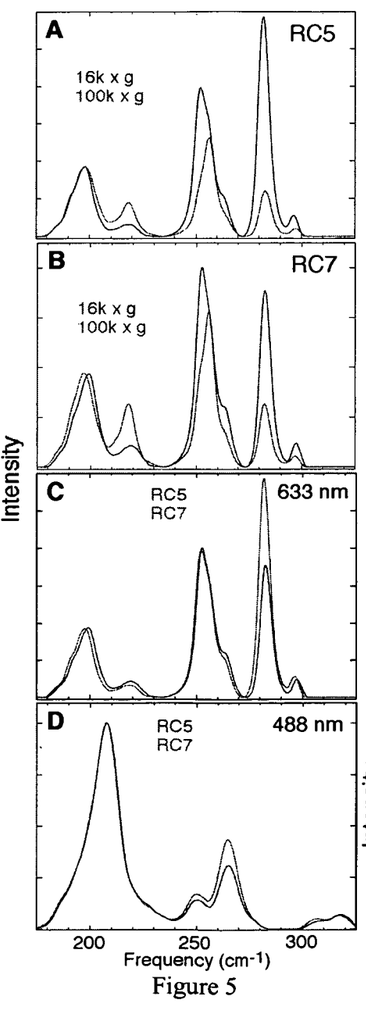

Raman Spectroscopy. Diameter selection is further substantiated by Raman spectroscopy of samples centrifuged at different speeds. Centrifugation should remove CNT bundles that are not diameter selected by RCP wrapping. Therefore, following centrifugation, the diameter distribution of individual SWNTs that are wrapped and maintained in solution by the RCPs can be analyzed. At a constant excitation wavelength (either 633 or 488 nm; 488 nm excitation data not shown), the radial breathing modes (RBMs) of the Raman spectra show intensity changes as a function of centrifugation speed (see FIGS. 5A and 5B). The same bands were observed in dispersions centrifuged at 16 k×g and 100 k×g; however, the relative intensities depended on the peptide. For the 633 nm excitation, for example, the bands at 252, 282 and 296 $cm^{-1}$ (corresponding to SWNTs with approximate diameters between 0.79 and 0.94 nm (26, 27)) are significantly enhanced as the RC5 sample is spun faster, whereas the band at 218 $cm^{-1}$ (~1.1 nm diameter SWNTs) is decreased in intensity (FIG. 5A). A similar pattern is observed for the RC7/SWNT dispersion (FIG. 5B); however, whereas the 252 and 282 $cm^{-1}$ bands invert their relative intensities for the RC5 sample at faster centrifugation speeds, the relative intensities in the RC7/SWNT dispersion remain similar. Similar patterns are also observed for the RBMs at a 488 nm excitation (data not shown).

FIGS. 5A to 5D are graphs of (5A and 5B) Raman RBM regions of RC5/SWNT (5A) and RC7/SWNT (5B) dispersions (red, 16 k×g, 20 min; blue, 100 k×g, 1 hr; 633 nm excitation). FIGS. 5C and 5D are comparisons of RBM regions of RC5/SWNT (red) and RC7/SWNT (blue) dispersions excited at 633 nm (5C) and 488 nm (5D). All spectra were normalized to the band at ~200 $cm^{-1}$.

Figure 6:
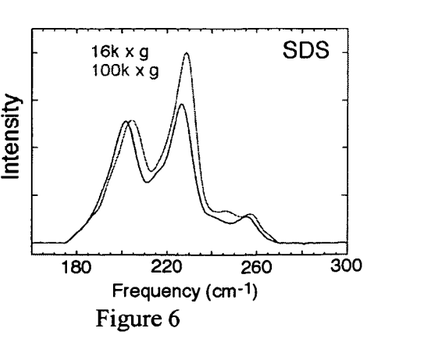
FIG. 6 is a graph of the Raman RBM regions of SDS/SWNT dispersion (red, 16 k×g, 20 min; blue, 100 k×g, 1 hr; 633 nm excitation)

The Raman results at different centrifugation speeds suggest a selective enhancement of smaller diameter SWNTs as the samples are spun faster, with a more significant enhancement occurring for RC5, evidence that smaller diameter SWNTs are enriched in the RC5 samples. If this effect were due simply to decreasing the concentration of the more dense CNTs in solution at higher speeds (and not to a diameter-selective solubilization), then t a decrease in the RBM features owing to the removal of the smaller diameter (more dense) CNTs would be expected, however, the opposite trend was observed. The densities associated with RC5/(11,3)-SWNT and RC7/(14,5)-SWNT systems were calculated based on our molecular models, including in each calculation all backbone atoms for a single RCP molecule and all carbon atoms in a 10 Å-long slice of a single SWNT; results of the calculations indicate that the smaller diameter RC5/(11,3)-SWNT system is ~6% more dense. For a control system in which diameter selection should not be observed, an SDS-solubilized HiPco CNTs was prepared and subjected to the same centrifugation procedure used for the RCP/SWNT preparations. As shown in FIG. 6, the RBM signals at higher wavenumbers are repressed in the 100 k×g sample, indicating that larger diameter CNTs are indeed retained.

FIG. 6 is a graph of the Raman RBM regions of SDS/SWNT dispersion (red, 16 k×g, 20 min; blue, 100 k×g, 1 hr; 633 nm excitation). Spectra were normalized to the band at ~200 $cm^{-1}$. A similar enhancement is observed at a fixed centrifugation speed (100 k×g) when comparing the RBMs for the RC5/SWNT and RC7/SWNT samples at both 633 and 488 nm excitations. The enhancement is seen for the 282 $cm^{-1}$ band in the RC5 sample at 633 nm (FIG. 5C) and for the 265 $cm^{-1}$ band in the RC5 sample at 488 nm (FIG. 5D). This demonstrates that the observed changes are not artifacts of a given excitation wavelength.

AFM Height Analysis. Support for diameter selection is also provided by AFM measurements conducted on the RCP/SWNT dispersions. With careful calibration of the scanner, height measurements can be used to accurately determine CNT diameters (18). RC5 and RC7 are expected to encircle SWNTs with diameters less than or equal to 1.15 and 1.49, respectively. If the peptide backbones of the RCPs are added to the SWNT diameters, the diameters are 1.86 nm (RC5/SWNTs) and 2.22 nm (RC7/SWNTs), respectively (FIG. 7A). Peptide side chains were not included in the calculated diameters because the AFM samples are dried; the side chains are expected to collapse onto the surface of the RCP/SWNT structure and not contribute significantly to the measured diameters.

AFM images of the RC5/SWNT and RC7/SWNT dispersions reveal well-dispersed SWNTs (FIG. 7B, C). The diameters of the CNTs do not appear completely uniform along their lengths. Rather, the CNTs exhibit smooth regions interrupted by brighter "beaded" areas. These features are possibly associated with bare CNTs (smooth regions) and peptide-wrapped segments (beaded areas). Diameter measurements were obtained at multiple points along each CNT in both the smooth and beaded areas (FIG. 7D). For the smooth regions, the diameter distribution for the RC7 sample is shifted significantly to higher diameters compared to the RC5 sample (FIG. 7E). The diameters range from 0.79 to 1.27 nm for the RC5/SWNT sample vs. 0.91 to 1.45 nm for the RC7/SWNT sample (Table 1). A test for unequal variances performed at the 95% confidence level revealed that the average diameters taken along smooth and beaded regions of a CNT can be distinguished between RC5/SWNT and RC7/SWNT samples (Table 1). Importantly, these diameter distributions are both significantly smaller than that observed for nano-1-wrapped HiPco SWNTs (18), suggesting that the RCPs solubilize CNTs with smaller diameters.

In the beaded regions, the measured diameters are significantly larger than those in the smooth regions. The measured diameters range from 1.41 to 1.79 nm for the RC5/SWNT sample and from 1.24 to 2.15 nm for the RC7/SWNT sample. These diameters are on average 0.47 and 0.61 nm larger than the smooth regions for RC5 and RC7, respectively, which is close to the expected value of 0.7 nm additional thickness for a single peptide backbone layer surrounding the CNT circumference (FIG. 7A). These AFM measurements strongly support our model for RCP wrapping of SWNTs, displaying diameter distributions consistent with diameter-selective solubilization.

FIG. 7A shows the expected dimensions for RC5/SWNT and RC7/SWNT structures. FIGS. 7B and 7C are 1.0×1.0 μm AFM images of diluted 100 k×g RC5/SWNT (7B) and RC7/SWNT (7C) dispersions. FIG. 7D (left) is an AFM height profile taken along the length of a single nanotube (7D, right AFM image, 0.5×0.5 μm), showing the differences between the smooth and beaded areas (beaded areas indicated by arrows). FIG. 7E shows the measured diameter distributions (smooth regions) for diluted 100 k×g RC5/SWNT and RC7/SWNT dispersions (n=100; four 2.0×2.0 μm images, two samples for each peptide).

TABLE 1

Statistical analysis of AFM height measurements.

| By Nanotube | RC5/SWNT | | RC7/SWNT | |
|---|---|---|---|---|
| | Smooth | Bead | Smooth | Bead |
| Mean (nm)$^a$ | 0.98 | 1.45 | 1.12 | 1.73 |
| Std. Dev. (nm) | 0.13 | 0.22 | 0.15 | 0.30 |
| Std. Dev. of Mean (nm) | 0.03 | 0.06 | 0.03 | 0.09 |
| Minimum (nm) | 0.79 | 1.41 | 0.91 | 1.24 |
| Maximum (nm) | 1.27 | 1.79 | 1.45 | 2.15 |
| n$^b$ | 17 | 15 | 20 | 11 |

$^a$For each individual nanotube, the mean values for the smooth and beaded regions were calculated. The entries in the table represent the average of the means determined for each nanotube. The height data were also analyzed by separately averaging all smooth and all beaded points for each RCP/SWNT sample (i.e. not calculating a mean for each nanotube), and the results were essentially identical to those reported in this table (not shown).
$^b$Number of nanotubes per AFM image. The n is different for smooth and beaded regions in a given RCP/SWNT sample because some nanotubes (2 for the RC5/SWNT sample; 9 for the RC7/SWNT sample) did not have beaded regions present (i.e. were completely smooth).

Limited Diameter Selection. Although RC5 appears to select, on average, smaller diameter SWNTs than RC7, the selection is not absolute (i.e., RBM bands corresponding to SWNTs larger than 1.0 nm diameter are present in both RCP samples, and a sharp diameter cutoff is not observed in the AFM data). One possible explanation is that the RCPs can polymerize, a known occurrence at high local RCP concentrations (data not shown). Although the peptide concentrations used in this study do not promote significant polymerization in solution, high local concentrations could form if multiple RCPs interacting with the same CNT were in close proximity on the tube surface. Oxidation could then lead to polymerization. Polymers composed of two or more RCP molecules would then be able to wrap SWNTs of various diameters, including those that were too large to be solubilized by cyclized RCP monomers (FIG. 8), thus providing a population of SWNTs in the RC5/SWNT dispersion with diameters larger than those allowed by cyclized RCPs.

Figure 8:
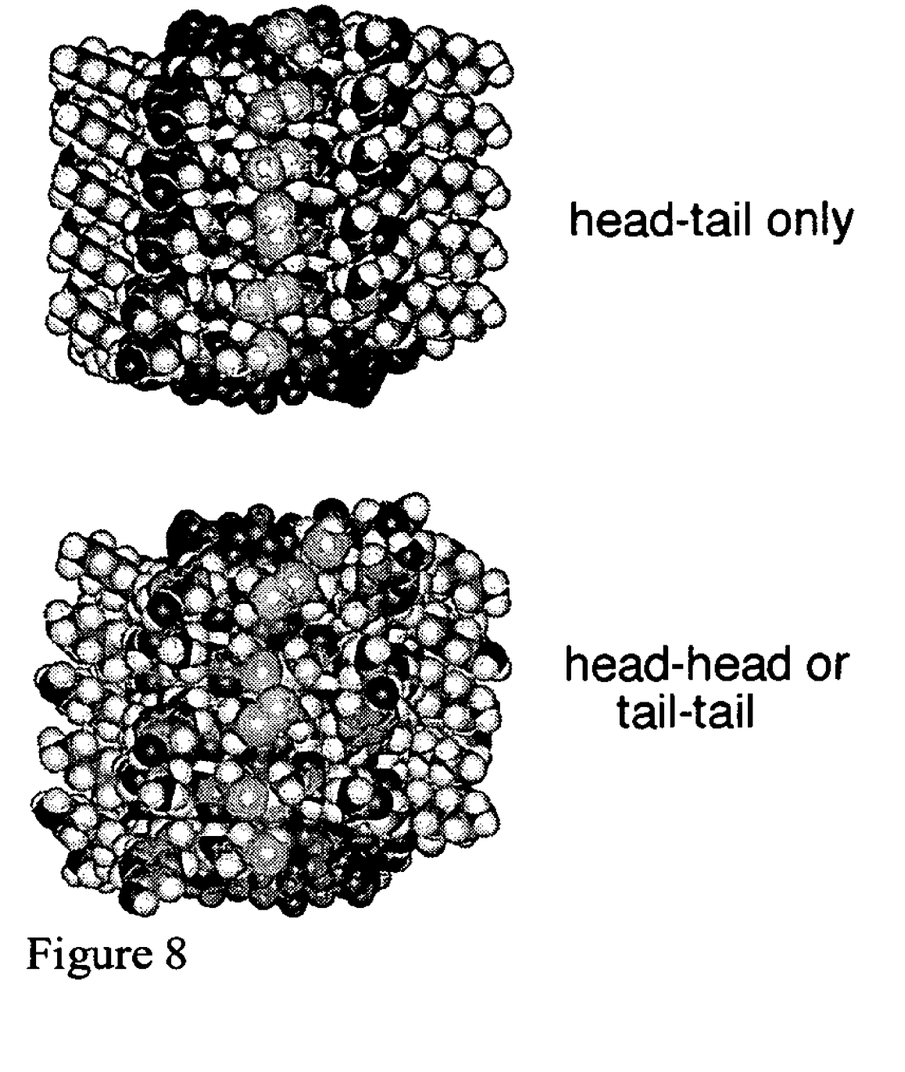
FIG. 8 shows two models showing possible polymerization of RCPs around SWNTs (C, green; H, white; N, blue; O, red; S, yellow; SWNT, pink)

FIG. 8 shows two models showing possible polymerization of RCPs around SWNTs (C, green; H, white; N, blue; O, red; S, yellow; SWNT, pink). A novel to coat SWNTs with reversible cyclic peptides that covalently close around CNTs was developed through oxidation of thiols incorporated into the peptide backbone. By controlling the length of the RCPs a limited diameter-selective solubilization of HiPco SWNTs was developed for SWNT purification. In addition, RCPs covalently closed around SWNTs do not dissociate from the SWNTs unless the disulfide bond is reduced. RCPs thus provide a platform to which other functional groups could be attached without disturbing the covalent structure of SWNTs.

The present invention includes a nanotube binding peptide comprising a cyclizable peptide that binds a single-walled carbon nanotube, wherein the cyclizable peptide comprises an N-terminus and a C-terminus that can be cyclized around the single-walled carbon nanotube, wherein the cyclizable peptide can be reversibly de-cyclized to release the single-walled nanotube, wherein the N-terminus and the C terminus form a noncovalent linkage within the peptide to create the closed ring structure that encircles the single-walled carbon nanotube.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES (1) Baughman, R. H.; Zakhidov, A. A.; de Heer, W. A. Science 2002, 297, 787-792.
(2) Moore, V. C.; Strano, M. S.; Haroz, E. H.; Hauge, R. H.; Smalley, R. E.; Schmidt, J.; Talmon, Y. Nano Lett. 2003, 3, 1379-1382.
(3) Dalton, A. B.; Blau, W. J.; Chambers, G.; Coleman, J. N.; Henderson, K.; Lefrant, S.; McCarthy, B.; Stephan, C.; Byrne, H. J. Synth. Met. 2001, 121, 1217-1218.
(4) O'Connell, M. J.; Boul, P.; Ericson, L. M.; Huffman, C.; Wang, Y. H.; Haroz, E.; Kuper, C.; Tour, J.; Ausman, K. D.; Smalley, R. E. Chem. Phys. Lett. 2001, 342, 265-271.
(5) Dieckmann, G. R.; Dalton, A. B.; Johnson, P. A.; Razal, J.; Chen, J.; Giordano, G. M.; Munoz, E.; Musselman, I. H.; Baughman, R. H.; Draper, R. K. J. Am. Chem. Soc. 2003, 125, 1770-1777.
(6) Wang, S.; Humphreys, E. S.; Chung, S.-Y.; Delduco, D. F.; Lustig, S. R.; Wang, H.; Parker, K. N.; Rizzo, N. W.; Subramoney, S.; Chiang, Y.-M.; Jagota, A. Nat. Mat. 2003, 2, 196-200.
(7) Zheng, M.; Jagota, A.; Semke, E. D.; Diner, B. A.; Mclean, R. S.; Lustig, S. R.; Richardson, R. E.; Tassi, N. G. Nat. Mat. 2003, 2, 338-342.
(8) Zheng, M.; Jagota, A.; Strano, M. S.; Santos, A. P.; Barone, P.; Chou, S. G.; Diner, B. A.; Dresselhaus, M. S.;

Mclean, R. S.; Onoa, G. B.; Samsonidze, G. G.; Semke, E. D.; Usrey, M. L.; Walls, D. J. Science 2003, 302, 1545-1548.

(9) Duesberg, G. S.; Muster, J.; Krstic, V.; Burghard, M.; Roth, S. Appl. Phys. A: Mater. Sci. Process. 1998, 67, 117-119.

(10) Duesberg, G. S.; Blau, W.; Byrne, H. J.; Muster, J.; Burghard, M.; Roth, S. Syn. Met. 1999, 103, 2484-2485.

(11) Doom, S. K.; Fields, R. E., III; Hu, H.; Hamon, M. A.; Haddon, R. C.; Selegue, J. P.; Majidi, V. J. Am. Chem. Soc. 2002, 124, 3169-3174.

(12) Farkas, E.; Anderson, M. E.; Chen, Z. H.; Rinzler, A. G. Chem. Phys. Lett. 2002, 363, 111-116.

(13) Doom, S. K.; Strano, M. S.; O'Connell, M. J.; Haroz, E. H.; Rialon, K. L.; Hauge, R. H.; Smalley, R. E. J. Phys. Chem. B 2003, 107, 6063-6069.

(14) Strano, M. S.; Zheng, M.; Jagota, A.; Onoa, G. B.; Heller, D. A.; Barone, P. W.; Usrey, M. L. Nano Lett. 2004, 4, 543-550.

(15) Heller, D. A.; Mayrhofer, R. M.; Baik, S.; Grinkova, Y. V.; Usrey, M. L.; Strano, M. S. J. Am. Chem. Soc. 2004, 126, 14567-14573.

(16) Boul, P. J.; Liu, J.; Mickelson, E. T.; Huffman, C. B.; Ericson, L. M.; Chiang, I. W.; Smith, K. A.; Colbert, D. T.; Hauge, R. H.; Magrave, J. L.; Smalley, R. E. Chem. Phys. Lett. 1999, 310, 367-372.

(17) Chattopadhyay, D.; Galeska, I.; Papadimitrakopoulos, F. J. Am. Chem. Soc. 2003, 125, 3370-3375.

(18) Zorbas, V.; Ortiz-Acevedo, A.; Dalton, A. B.; Yoshida, M. M.; Dieckmann, G. R.; Draper, R. K.; Baughman, R. H.; Jose-Yacaman, M.; Musselman, I. H. J. Am. Chem. Soc. 2004, 126, 7222-7227.

(19) Ghadiri, M. R.; Granja, J. R.; Milligan, R. A.; McRee, D. E.; Khazanovich, N. Nature 1993, 366, 324-327.

(20) Bong, D. T.; Clark, T. D.; Granja, J. R.; Ghadiri, M. R. Angew. Chem. Int. Ed. 2001, 40, 988-1011.

(21) Ortiz-Acevedo, A.; Dieckmann, G. R. Tet. Lett. 2004, 45, 6795-6798.

(22) Nikolaev, P.; Bronikowski, M.; Bradley, R.; Rohmund, F.; Colbert, D.; Smith, K.; Smalley, R. E. Chem. Phys. Lett. 1999, 313, 91-97.

(23) Okamoto, H.; Nakanishi, T.; Nagai, Y.; Kasahara, M.; Takeda, K. J. Am. Chem. Soc. 2003, 125, 2756-2769.

(24) Ellman, G. L.; Courtney, K. D.; Andres, V., Jr.; Feather-Stone, R. M. Biochem. Pharmacol. 1961, 7, 88-95.

(25) Nagahara, L. A.; Hashimoto, K.; Fujishima, A. J. Vac. Sci. Technol. B. 1994, 12, 1694-1697.

(26) Bachilo, S. M.; Strano, M. S.; Kittrell, C.; Hauge, R. H.; Smalley, R. E.; Weisman, R. B. Science 2002, 298, 2361-2366.

(27) Karachevtsev, V. A.; Glamazda, A. Y.; Dettlaff-Weglikowska, U.; Kumosov, V. S.; Obraztsova, E. D.; Peschanskii, A. V.; Eremenko, V. V.; Roth, S. Carbon 2003, 41, 1567-1574.

What is claimed is:

1. A method of capturing single-walled carbon nanotubes comprising the steps of:
   mixing single-walled carbon nanotubes with one or more de-cyclizable peptides comprising at least two thiol groups wherein the peptides comprise $R_1$—Y($^D$AK)$_4$$^D$AQNH—$R_2$ (SEQ ID NO:1), wherein $R_1$ and $R_2$ comprise thiol groups.

2. A method of capturing single-walled carbon nanotubes comprising the steps of:
   mixing single-walled carbon nanotubes with one or more de-cyclizable peptides comprising at least two thiol groups, wherein the peptides comprise $R_1$—Y($^D$AK)$_6$$^D$AQNH—$R_2$ (SEQ ID NO:2), wherein $R_1$ and $R_2$ comprise thiol groups.

3. A nanotube binding peptide comprising:
   a cyclizable peptide that binds a single-walled carbon nanotube, wherein the cyclizable peptide comprises an N-terminus and a C-terminus that can be cyclized around the single-walled carbon nanotube, wherein the cyclizable peptide can be reversibly decyclized to release the single-walled nanotube, wherein the peptide contains 11 amino acids, wherein the peptide comprises $R_1$—Y($^D$AK)$_4$$^D$AQNH—$R_2$ (SEQ ID NO:1), and wherein $R_1$ and $R_2$ comprise thiol groups.

4. A nanotube binding peptide comprising:
   a cyclizable peptide that binds a single-walled carbon nanotube, wherein the cyclizable peptide comprises an N-terminus and a C-terminus that can be cyclized around the single-walled carbon nanotube, wherein the cyclizable peptide can be reversibly decyclized to release the single-walled nanotube, wherein the peptide contains 15 amino acids, wherein the peptide comprises $R_1$—Y($^D$AK)$_6$$^D$AQNH—$R_2$ (SEQ ID NO:2), and wherein $R_1$ and $R_2$ comprise thiol groups.

* * * * *